US005112322A

United States Patent [19]

Hathaway

[11] Patent Number: 5,112,322

[45] Date of Patent: May 12, 1992

[54] EMESIS HEAD APPLIANCE

[75] Inventor: Lucille Hathaway, 1229 Azalea Ct. West, Melbourne, Fla. 32935

[73] Assignee: Lucille Hathaway, Melbourne, Fla.

[21] Appl. No.: 600,616

[22] Filed: Oct. 19, 1990

[51] Int. Cl.[5] .............................................. A61M 1/00

[52] U.S. Cl. .......................... 604/317; 128/DIG. 24; 128/863; 604/331; 433/137

[58] Field of Search ................ 128/857, 859, 860-863, 128/DIG. 24; 604/317, 327, 331; 383/28, 35, 36, 99; 433/136, 137

[56] References Cited

U.S. PATENT DOCUMENTS 2,943,660 7/1960 Seeger ........................ 128/DIG. 24
3,315,672 4/1967 Cunningham et al. ............. 128/863
3,438,370 4/1969 Krantz ................................ 128/863
3,920,179 11/1975 Hall .................................. 383/12 X
4,182,478 1/1980 Ebes ..................................... 383/28

FOREIGN PATENT DOCUMENTS 0895252 11/1953 Fed. Rep. of Germany ...... 128/863

*Primary Examiner*—Robert A. Hafer
*Assistant Examiner*—Brian E. Hanlon
*Attorney, Agent, or Firm*—Evenson, Wands, Edwards, Lenahan & McKeown

[57] ABSTRACT

An emesis head appliance is made of clear flexible plastic or disposable material. The appliance includes a two-piece basin sized and configured to receive discharge from a patient and to fit snugly under the chin with side panels reaching upward to the temple area. A drainage tube of sufficient length is attached to the lower end of the basin to act as an outlet for disposing of the discharge waste. A slide clamp is attachable to the tube and closes the tube to prevent leakage until it is desired to discharge the waste material in the basin.

20 Claims, 2 Drawing Sheets

EMESIS HEAD APPLIANCE

BACKGROUND AND SUMMARY OF THE INVENTION

The present invention relates to an emesis head appliance and, more particularly, to a two-piece leak proof emesis head appliance which offers a more sanitary and convenient way of caring for cases of nausea and vomiting, nasal irrigations, oral care and the like.

Prior to the present invention, there was no sanitary, convenient and inexpensive way of dealing with cases of nausea and vomiting which could be carried on a person or patient and which could either be disposable or reusable when proper attention is given to care and cleanliness.

It is an object of the present invention to provide an emesis head appliance which offers a more sanitary and convenient way of caring for cases of nausea and vomiting, nasal irrigation, oral care and the like which can be used for patients in a reclining position or in any degree of head elevation.

It is another object of the present invention to provide a head appliance which can be folded into a small compact package and can be carried in a pocket or purse so as to be able to deal with cases of nausea and vomiting wherever they may occur, e.g. in a moving vehicle.

It is yet further object of the present invention to provide a disposable or selectively reusable head appliance which can be made with its size proportioned to a head or with one size fitting all patients.

The foregoing objects have been achieved in accordance with the present invention by constructing the emesis head appliance in the form of a two-piece leak proof clear flexible plastic bag which fits snugly under the chin with side panels reaching upwardly to the temple providing protection for the ears and the hair. The appliance in accordance with the present invention secures itself on the head with a pair of tie strings or, alternatively, an elastic band. Moreover, a belt or other adjustment device can be provided to lengthen or shorten the elastic band so as to make the same adjustable. Tie strings may serve in conditions where adjustment is needed to allow free circulation to the scalp.

According to another aspect of the present invention, the two-piece appliance forms a basin slightly elongated to prevent spillage. The basin is configured and sized to allow enough space for free breathing and proper distance between the face and the rim of the basin, and can also be calibrated for accurate measurement where fluid intake and output is desirable or necessary for medical reasons.

Yet another feature of the present invention provides a two-piece reinforcement for added strength to the part fitting under the chin inasmuch as I have found that body temperature may tend to cause flexible plastic to soften and rumple.

Still another feature of the present invention is a drainage tube of sufficient length integrated to the lower end of the basin for a disposal outlet. A slide clamp can be attached to the tube and be placed close to the lower end of the basin at all times in readiness to be clamped when needed in an emergency. It is contemplated that the clamp will be a separate item from the appliance and can be of any type which serves the purpose of closing the tube so as to be sufficiently leak proof.

The advantage of the present invention as described above is that it can be folded into a small compact package and carried in a pocket or purse. It can be made from material other than plastic so as to be disposable, but can also be reusable where proper attention is given to care and cleanliness. The appliance can be made so that one size fits all, i.e. universal fit, or it can be made so as to be proportioned to the face of the wearer, e.g. a child or an adult.

BRIEF DESCRIPTION OF THE DRAWINGS

These and other objects, advantages and novel features of the present invention will become more apparent from the following detailed description of a presently preferred embodiment when taken in conjunction with the accompanying drawing wherein.

DETAILED DESCRIPTION OF THE DRAWINGS

Figure 2:
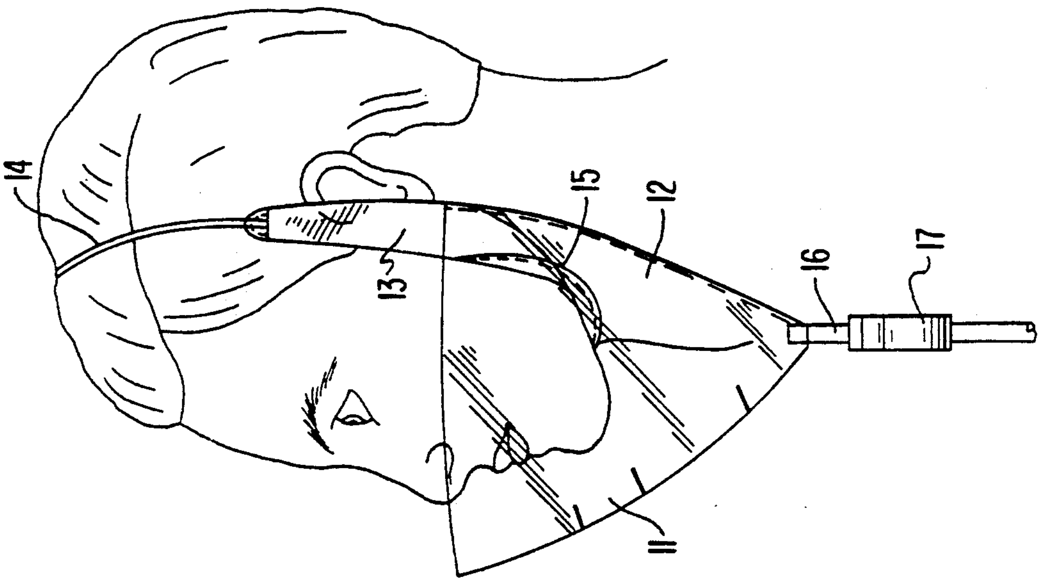
FIG. 2 is a side view of the emesis head appliance shown in FIG. 1 on a patient's head.
Figure 1:
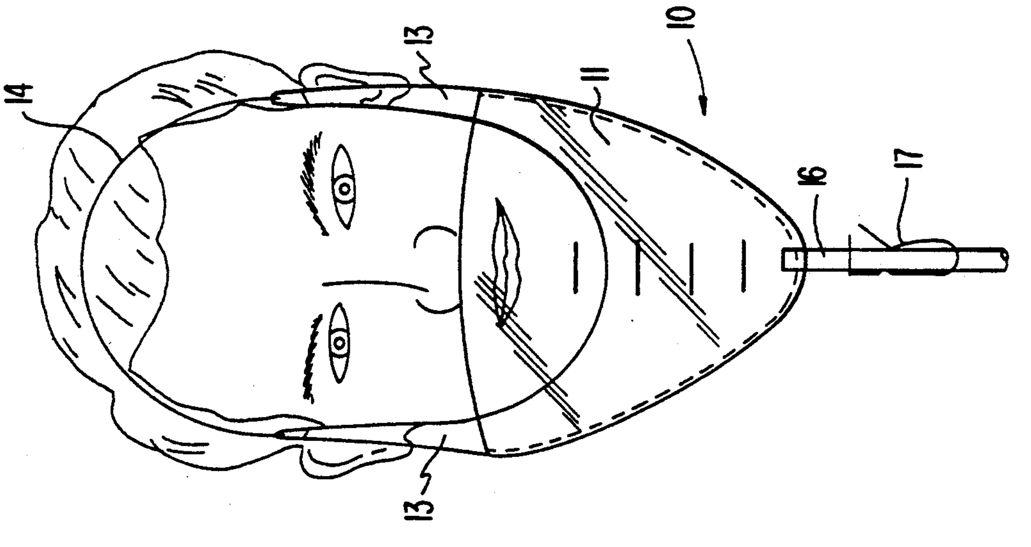
FIG. 1 is a front view of the emesis head appliance made in accordance with the present invention as applied to a patient's head.
Figure 4:
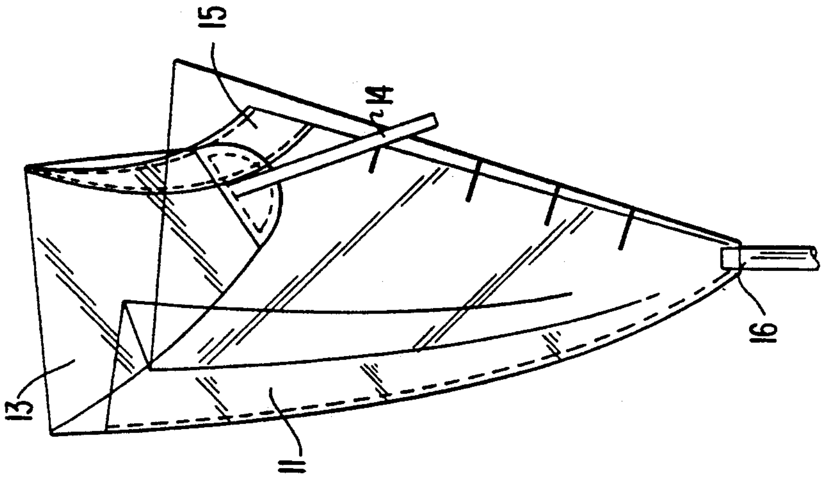
FIG. 4 is a view of the emesis head appliance of FIGS. 1 and 2 shown in the folded position with the side panels folded down for carrying in a pocket or purse.
Figure 3:
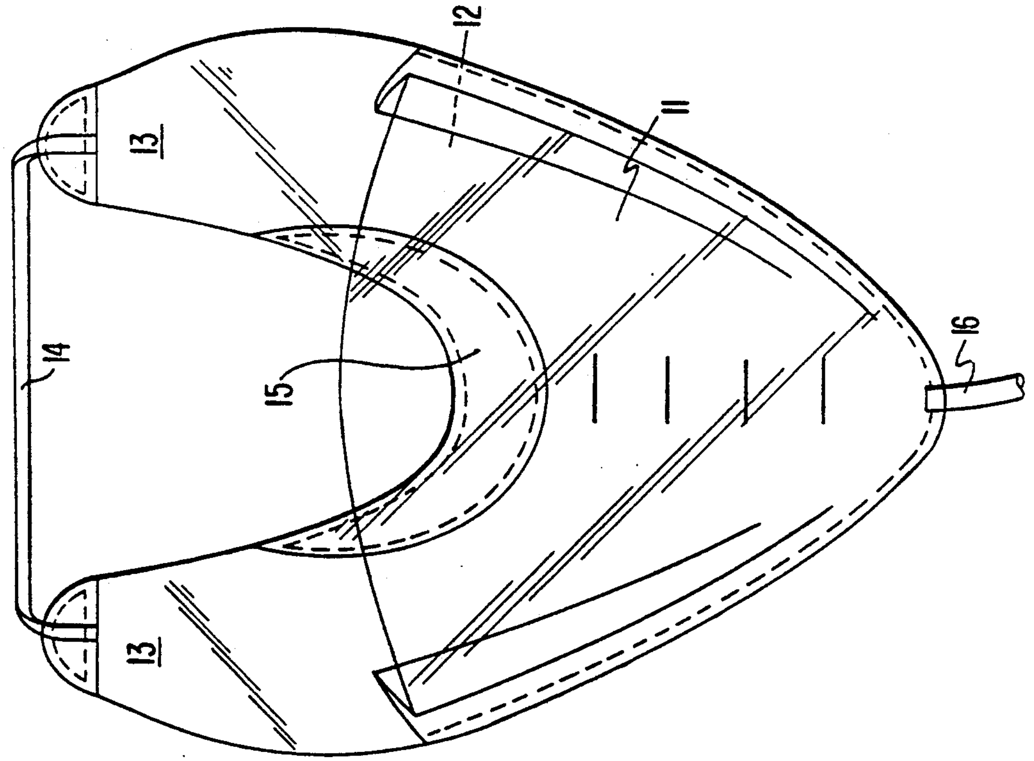
FIG. 3 is a front view of the appliance shown in FIGS. 1 and 2 but with the front piece folded flat against the rear piece.

The emesis head appliance according the present invention shown in FIGS. 1 and 2 on the patient's head is designated generally by the numeral 10. It comprises a basin formed on this particular embodiment of two pieces, namely a front piece 11 upon which calibrations shown by the horizontal lines in FIGS. 1 and 3 are imprinted and a rear piece 12 which has a cut out portion designed to fit under the chin and along the side of the wearer's head as shown in FIGS. 1 and 2.

The appliance 10 can be made out of a clear flexible plastic or can be made of a material which is more disposable such as a non-woven paper product. Side panels 13 on the rear piece 12 reach upwardly from the basin to the temple of the wearer so as to provide protection for the ears and the hair. The side panels 13 are secured to the head either with a pair of tie strings or with an elastic band 14 which can be adjustable. The tie strings 14 can be used in conditions where adjustment is needed to allow free circulation to the scalp.

The basin formed by front and rear pieces 11, 12 is constructed and sized so as to provide a slightly elongated cavity to prevent spillage of the discharge material. It also allows enough space for free breathing and a proper distance between the face of the wearer and the rim of the basin. As previously mentioned, the front panel 11 can be calibrated for accurate measurement where fluid intake and output is indicated for medical reasons.

A two-piece reinforcement 15 is added to the rear piece 12 for strengthening the basin to the portion fitting under the chin, i.e. one layer to each side of the wall of the rear piece 12, inasmuch as body temperature may cause flexible plastic to soften and rumple.

At the base of the basin, there is provided a drainage tube 16 of sufficient length for acting as a disposal outlet for the drainage material. A slide spring clamp 17 of known construction can be attached to the tube 15 and placed normally close to the lower end of the basin so as to be in readiness to be clamped when needed in an emergency. As shown in the present embodiment, the clamp 17 is a separate item from the appliance 10 and can be of any generally known type which serves the purpose of closing the tube 16 so that it is positively leak proof.

Although the invention has been described and illustrated in detail, it is to be clearly understood that the same is by way of illustration and example, and is not to be taken by way of limitation. The spirit and scope of the present invention are to be limited only by the term of the appended claims.

What is claimed:

1. A head appliance comprising head securing means, a non-rigid basin sized and configured to fit under and extend below a wearer's chin having sufficient volumetric capacity to prevent spillage of discharge from the wearer, side panels operatively connected with the basin and sized so as to extend upwardly to the wearer's temple and prevent the spillage of the discharge from contacting the wearer's head said side panels having inner and outer surfaces, said inner surfaces contacting the face of the wearer, said basin connected to said side panels at said outer surfaces so as to provide sufficient free breathing space defined by an opening between an upper free end of the basin and the face of the wearer in the regions of the wearer's nose, mouth and chin, and a selectively closable drainage tube arranged at a bottom region of the basin.

2. The head appliance according to claim 1, wherein the basin comprises two portions joined together.

3. The head appliance according to claim 1, wherein a portion of the basin in the region of the wearer's chin includes reinforcement.

4. The head appliance according to claim 1, wherein at least the basin is made of clear plastic.

5. The head appliance according to claim 4, wherein a portion of the basin in the region of the wearer's chin includes reinforcement.

6. The head appliance according to claim 1, wherein at least the basin is made of a foldable disposable material.

7. The head appliance according to claim 6, wherein the basin comprises two portions joined together.

8. The head appliance according to claim 1, wherein the securing means comprises tie strings.

9. The head appliance according to claim 1, wherein the securing means comprises an elastic band.

10. The head appliance according to claim 9, wherein means is operatively associated with the band for selectively lengthening and shortening the band.

11. The head appliance according to claim 1, wherein a portion of the basin opposite the wearer's chin is calibrated for accurate measurement of intake to and output from the wearer.

12. The head appliance according to claim 1, wherein a slide clamp is operatively associated with the drainage tube for the selective closing of the tube.

13. The head appliance according to claim 12, wherein a portion of the basin opposite the wearer's chin is calibrated for accurate measurement of intake to and output from the wearer.

14. The head appliance according to claim 13, wherein a portion of the basin in the region of the wearer's chin includes reinforcement.

15. The head appliance according to claim 14, wherein the basin comprises two portions joined together.

16. The head appliance according to claim 15, wherein at least the basin is made of clear plastic.

17. The head appliance according to claim 15, wherein at least the basin is made of a foldable disposable material.

18. The head appliance according to claim 15, wherein the securing means comprises tie strings.

19. The head appliance according to claim 15, wherein the securing means comprises an elastic band.

20. The head appliance according to claim 19, wherein means is operatively associated with the band for selectively lengthening and shortening the band.

* * * * *